US00PP22808P3

(12) United States Plant Patent
Korlipara

(10) Patent No.: US PP22,808 P3
(45) Date of Patent: Jun. 19, 2012

(54) ***ECHINACEA* PLANT NAMED 'MAUI SUNSHINE'**

(50) Latin Name: ***Echinacea* sp.**
Varietal Denomination: Maui Sunshine

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 296 days.

(21) Appl. No.: 12/798,840

(22) Filed: Apr. 12, 2010

(65) Prior Publication Data

US 2011/0252532 P1 Oct. 13, 2011

(51) Int. Cl.
*A01H 5/00* (2006.01)

(52) U.S. Cl. ..... Plt./428

(58) Field of Classification Search ..... Plt./428
See application file for complete search history.

(56) References Cited

U.S. PATENT DOCUMENTS

PP17,652 P2 * 4/2007 Saul ..... Plt./428
PP19,464 P2 * 11/2008 Korlipara ..... Plt./428
PP21,811 P2 * 3/2011 van den Aardwegh ..... Plt./428

OTHER PUBLICATIONS

UPOV ROM GTITM Computer Database, GTI Jouve Retrieval Software 2011/10 Citation for 'Maui Sunshine'.*

* cited by examiner

*Primary Examiner* — Wendy C Haas
(74) *Attorney, Agent, or Firm* — Klarquist Sparkman, LLP

(57) ABSTRACT

A new and distinct *Echinacea* plant named 'Maui Sunshine' characterized by large, bright yellow flowers with multiple ray florets, ray florets held perpendicular to the stem, well-branched flower stalks, a medium tall habit, and excellent vigor.

1 Drawing Sheet

Botanical denomination: *Echinacea* sp.

Variety designation: 'Maui Sunshine'.

The present invention relates to a new and distinct cultivar of *Echinacea* and given the cultivar name 'Maui Sunshine'. *Echinacea* is in the family Asteraceae. This new cultivar originated as a fourth generation seedling from a planned breeding program using the unpatented parents *Echinacea paradoxa* and *Echinacea purpurea* 'Ruby Giant' for the initial cross. The exact parents of this selection are unnamed proprietary, unreleased plants.

Compared to *Echinacea* 'Ruby Giant', an unpatented plant and the original seed parent in the breeding line, the new variety has yellow rather than red purple flowers.

Compared to *Echinacea paradoxa,* an unpatented plant and the original pollen parent in the breeding line, the new variety is shorter, with ray florets held on the horizontal rather than drooping and green cones with yellow orange bracts rather than brown cones with brown bracts.

Compared to *Echinacea* 'Mac 'n' Cheese', U.S. Plant Pat. No. 19,464, the new variety is taller with yellow flowers rather than yellow orange flowers.

This new *Echinacea* cultivar is distinguished by:

1. large, bright yellow flowers with multiple ray florets
2. ray florets held perpendicular to the stem
3. well-branched flower stalks
4. medium tall habit
5. excellent vigor This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows *Echinacea* 'Maui Sunshine' growing in the ground in full sun in the test field in late July in Canby, Oreg.

DETAILED PLANT DESCRIPTION

The following is a detailed description of the new *Echinacea* cultivar based on observations of 18-month-old specimens growing in the ground in the field in full sun in the trial bed under typical outdoor conditions in Canby, Oreg. The plants had been moved from one trial field to another the fall before. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, fifth edition.

Plant:

*Type.*—Herbaceous perennial.

*Hardiness.*—USDA Zones 4 to 9.

*Size.*—Grows to 70 cm wide and 90 cm tall to top of flowers.

*Form.*—Basal clump.

*Vigor.*—Excellent.

*Roots.*—Roots develop easily from cuttings from the crown.

Stem (flowering):

*Type.*—Ascending.

*Size.*—Branching 0 to 3 times to 90 cm tall to a terminal flower and 7 mm wide at base.

*Number of stems from the crown.*—18.

*Internode length.*—3 to 9 cm.

*Surface texture.*—Strigose.

*Color.*—Green 138A mottled with Yellow Green 145B.

Leaf (basal):

*Type.*—Simple.

*Shape.*—Lanceolate.

*Arrangement.*—Basal.

*Blade size.*—Grows to 15 cm long and 6 cm wide.

*Margins.*—Shallowly broadly serrate.

*Apex.*—Acute.

*Base.*—Attenuate, continuing down petiole near the blade, clasping.

*Surface texture.*—Strigose on both sides.

*Venation.*—Pinnate.

*Color.*—Topside, Yellow Green 147A with the vein Yellow Green 147D and bottom side closest to Yellow Green 147A with the vein Yellow Green 147D.

*Petiole description.*—Grows to 20 cm long and 4 mm wide, glabrous, Yellow Green 147B.

Leaf (stem):

*Type.*—Simple.

*Shape.*—Lanceolate.

*Arrangement.*—Alternate.

*Blade size.*—Grows to 11.5 cm long and 4 cm wide.

*Margins.*—Slightly undulate and entire.

*Apex.*—Acute to acuminate.

*Base.*—Attenuate, continuing down petiole, clasping.

*Surface texture.*—Strigose on both sides.

*Venation.*—Pinnate.

*Color.*—Topside, Yellow Green 147A with the vein Yellow Green 146D and bottom side closest to Yellow Green 147B with the vein Yellow Green 146D.

*Petiole description.*—Grows to 5 cm long and 4 mm wide, strigose, Yellow Green 146B.

Inflorescence:

*Type.*—Composite on terminal stalked heads.

*Number of flowering stems per plant in summer.*—18.

*Flowering stem.*—Grows to 85 cm tall from the base of the plant to the terminal flower and can grow to 23 cm long from the top leaf to the base of a flower head; branched, 1 to 4 flowers per stem; diameter growing to 8 mm wide near the flower head; strigose, Green 138A mottled with Yellow Green 145B.

*Size.*—Grows to 11 cm wide and 4.5 cm deep as disc enlarges.

*Form.*—Ray florets held mostly perpendicular to the stem, some dropping down slightly; mature disc is conic.

*Immature inflorescence.*—3.8 cm wide and 2.3 cm deep, ray florets held at a 45 degree angle and rolled up so only the back color shows, Yellow 3C except on inside tip where Yellow Green N144A; disc is Yellow Green 146A.

*Ray florets.*—Without pistil or stamen, 28 to 32 in number, oblanceolate with the tip cupped and 1 to 3 toothed (each acute), entire margins, base attenuate, grows to 4 cm long and 8 mm wide, glabrous on both sides; topside color Yellow 11A; bottom side closest to Green Yellow 1C.

*Disc.*—Slightly convex becoming conic, becoming 40 mm long and 43 mm wide with maturity, color Yellow Orange 14A.

*Disc florets.*—About 400 in number, each 10 mm long and 1.5 mm wide, each with one persistent, very stiff bract (13 mm long and Orange 17A on top ⅓, Yellow Green 146A on middle ⅓, White NN155B on bottom ⅓); corolla 4 mm long and 1 mm wide, 5 lobed, glabrous, Yellow Green 145C, pistil 11 mm long, ovary 4 mm long, White NN155A, style 5 mm long Yellow Green 145D, with an extruding, 2-branched stigma spreading 3.5 mm wide, Yellow Green 145B; stamen 4 in number, 6 mm long, anthers 2.5 mm long and Greyed Purple N186A, filaments 3.5 mm long, Yellow Green 145D, pollen Yellow Orange 15A.

*Phyllaries.*—In 4 leafy series, area 3.5 cm wide and 6 mm deep, lobes lanceolate in shape, reflexed, grow to 10 mm long and 2 mm wide, margins strigose, tip acute, Yellow Green 147B.

*Receptacle.*—Grows to 14 mm wide and 17 mm deep, White 155B.

*Bloom period.*—July through October in Canby, Oreg.

*Fragrance.*—Lovely, floral.

*Lastingness.*—Each inflorescence lasts about two weeks in Canby, Oreg.

Seeds: Average number of 7 seeds/head, each 5 mm long and 2.5 mm wide, oval, Brown 200C.

*Fertility.*—Good.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

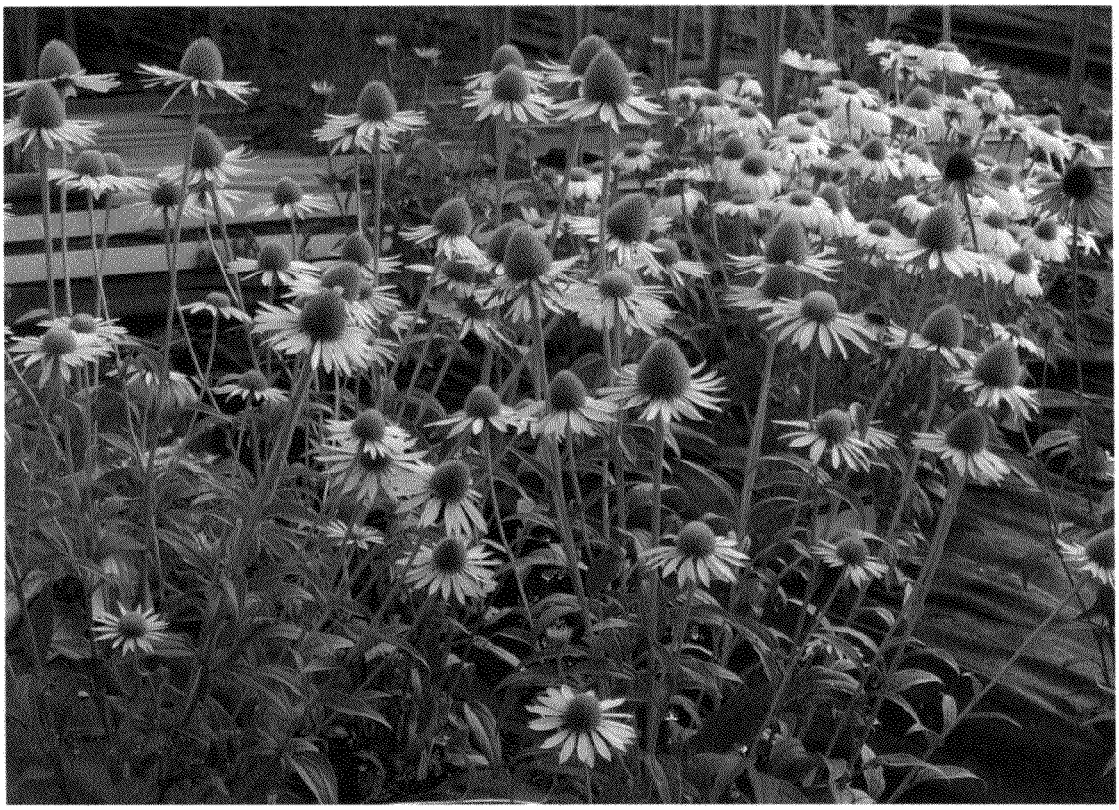

* * * * *